United States Patent [19]

Binder

[11] Patent Number: 5,714,468
[45] Date of Patent: Feb. 3, 1998

[54] METHOD FOR REDUCTION OF MIGRAINE HEADACHE PAIN

[76] Inventor: William J. Binder, 1640 Amalfi Dr., Pacific Palisades, Calif. 90272

[21] Appl. No.: 588,654

[22] Filed: Jan. 19, 1996

Related U.S. Application Data

[63] Continuation of Ser. No. 343,331, Nov. 21, 1994, abandoned, which is a continuation-in-part of Ser. No. 240,973, May 9, 1994, abandoned.

[51] Int. Cl.$^6$ .................... A61K 38/10; A61K 38/04
[52] U.S. Cl. .................................... 514/14; 514/2
[58] Field of Search ................................ 514/14, 2

[56] References Cited

FOREIGN PATENT DOCUMENTS

WO9305800   4/1993   WIPO.

OTHER PUBLICATIONS

Physicians' Desk Reference, pp. 792–797, 1994.
Olosen, *Clinical and pathophysiological observations in migraine and tension–type headach explained by integration of vacsular, supraspinal and myofascial inputs*, Elsevier Science Publishers B.V. vol. 46, pp. 125–129, 1991.
Blitzer, et al., Abstract Title, *The management of Hyperfunctional lines with Botulinum Toxin: A Collaborative study of 200 patients*, 1993.
Borodic, et al., *Botulinum A toxin for treatment of Aberrant facial nerve regenration*, P & R Surgery, May 1993, vol. 91, No.6 pp. 1042–1045.
Borodic, et al., *Botulinum A Toxin for the treatment of Adult–Onset Spasmodic Torticollis*, P & R Surgery Feb. 1991, vol. 87, No. 2, pp. 285–289.
Jankovic, et al., *Therapeutic uses of Botulinum Toxin*, New England Journal of Medicine, Apr. 25, 1991, 324:1186–1194.
Keen, et al., *Botulinum Toxin for Hyperkinetic Facial Lines: Results of a Double Placebo Controlled Study*, Jan. 15, 1993, Presented in Part at the Winter Meeting of the American Academy of Facial Plastic and Reconstructive Surgery, Boca Raton, Florida.
Anderson et al, *Medline Abstracts*, abstract No. 93059130, 1992.
Jedynak et al, *Biological Abstracts*, vol. 90, No. 7, abstract No. 79336, 1990.
Yakovleff et al., *Biological Abstracts*, vol. 97, No. 3, abstract No. 33434, 1993.

*Primary Examiner*—William R. A. Jarvis
*Attorney, Agent, or Firm*—Chadbourne & Parke LLP

[57] ABSTRACT

The invention is a method for reducing headache pain and symptoms associated with the onset or occurrence of headache in mammals. The method is performed by delivering an invertebrate presynaptic neurotoxin to a mammal extramuscularly (preferably at a localized, site of pain), or at a site in one or more muscles (preferably muscles of the face, cranium and neck). The presynaptic neurotoxins administered according to the invention are those neurotoxins that are known to produce a reversible, flaccid paralysis of muscle tissue in mammals. The preferred neurotoxin for use in the method of the invention is Botulinum toxin, particularly Botulinum toxin A.

21 Claims, 1 Drawing Sheet

METHOD FOR REDUCTION OF MIGRAINE HEADACHE PAIN

RELATED PATENT APPLICATIONS

This is a continuation of application Ser. No. 08/343,331 filed on Nov. 21, 1994, now abandoned, which is a continuation-in-part of U.S. patent application Ser. No. 81/240,973, filed May. 9, 1994, now abandoned.

BACKGROUND OF THE INVENTION

1. Field of the Invention

The invention relates to the pharmacological treatment of headache pain. More specifically, the invention relates to the reduction of pain associated with headaches through localized administration of a therapeutically effective dosage of pharmaceutically safe invertebrate exotoxin, in particular Botulinum toxin A.

2. History of the Prior Art

"Headache" is a term which encompasses a relatively vast spectrum of common symptoms and sometimes obscure causes. Headaches may be associated with emotional states such as depression and tension, as well as physical events such as muscular tension, neuralgia, neuropathy and vascular disturbances. Although a patient may experience more than one kind of headache pain, the various manifestations of headache are generally believed to have different pathological origins. (but see, Olosen, et al., *Pain*, 46:125–132, 1991 [a model, albeit one unaccepted in the art, which proposes that tension headache shares a causal myofascial component with migraine]). For example, it is generally accepted in the art that the headache condition known as migraine is directly related to vascular changes and events attributable to contraction of the smooth muscles of blood vessels (see, e.g., Wolff, et al., "Headache and Other Head Pain", 1963; and Table 1(a), Row 1), while tension headache originates in skeletal (striated) muscular stress (Table 1(a), Row 2) and other headache pain stems principally from neurological disorders (see, e.g., Table 1(b)). Although therapies intended to alleviate headache symptoms are abundant, the efficacy of such treatments varies widely.

The most common types of headache, together with the perceived pathological origin of the pain and conventional methods for treatment, are summarized in Tables 1(a)–(b) below:

TABLE 1(a)

HEADACHES NOT PRIMARILY ASSOCIATED WITH DISORDERS OF THE FACIAL AND CRANIAL NERVES

| Type | Presumed Mechanism | Site | Common Treatment |
|---|---|---|---|
| Migraine (vascular headache) | Vascular dilation resulting in changes to cerebral blood flow; possible hormonal origin | Fronto temporal (uni- or bilateral) | Ergot preparations, analgesic, anti-inflammatory medications, and serotonin modulators |
| Tension headache | Vascular disturbance and muscle spasm or fatigue (the latter is not believed to be the primary origin of pain) | Generalized | Analgesic, anti-inflammatory, anti-anxiety and anti-depressant medication |

TABLE 1(a)-continued

HEADACHES NOT PRIMARILY ASSOCIATED WITH DISORDERS OF THE FACIAL AND CRANIAL NERVES

| Type | Presumed Mechanism | Site | Common Treatment |
|---|---|---|---|
| Meningeal irritation | Meningitis | Generalized | Treat the underlying disease |
| Brain tumor | Cancer | Varies | Treat the underlying disease |
| Temporal arteritis | Arterial disorders | Unilateral, temporal, occipital | Corticosteroids |
| Traumatic headache | Head injuries resulting in subdural hematoma, dysautonomic cephalalgia or other disorders | Varies depending on origin | Varies depending on origin |

TABLE 1(b)

HEADACHES PRIMARILY ASSOCIATED WITH DISORDERS OF THE FACIAL AND CRANIAL NERVES

| Trigeminal neuralgia | Trigeminal nerve, unilateral | Idiopathic, vascular disturbances, multiple sclerosis, tumor | Carbamazepine |
|---|---|---|---|
| Atypical facial neuralgia | Unilateral or bilateral | Depressive, anxiety states, idiopathic | Anti-depressant and anti-anxiety medication |
| Orbitally related neuralgias | Unilateral in eye, cheek, ear, neck | Idiopathic, parasinus disorders | Decongestant nasal medication |
| Tolosa-Hunt Syndrome | Unilateral, mainly orbital | Arteritis and granulomatous lesions | Corticosteroid therapy |
| Reader's paratrigeminal syndrome | Unilateral, fronto-temporal and maxilla | Tumors, granulomatous lesions | Varies depending on origin |
| Postzoster syndrome | Unilateral, trigeminal divisions | Herpes zoster | Carbamazepine and anti-depressants |
| Costen's syndrome | Unilateral, near temporomandibular joints | Loss of teeth, rheumatoid arthritis | Bite correction, arthritis related therapies |

(Tables 1(a) and 1(b) are adapted from *Harrison's Principles of Internal Medicine,* 11th Ed., Chapter 6, Tables 6-1 and 6-2 (McGraw-Hill, 1987)).

One therapeutic modality for certain neuromuscular disorders which has begun to gain acceptance in recent years is the administration of invertebrate exotoxins in a pharmaceutically safe form. For example, serotype A of the Botulinum toxin has been recommended in the art for use for the treatment of certain diseases such as disorders of the extraocular muscles (e.g., comitant strabismus and nystagmus) as well as dystonias (involuntary contractions of facial muscle) (see, e.g., The *New England Journal of Medicine,* 324:1186–1194, 1991). The advantage of using Botulinum toxin A in this context is that it produces a reversible, flaccid paralysis of mammalian skeletal muscle, presumably by blocking the exocytosis of acetylcholine at peripheral, presynaptic cholinergic receptors, with limited activity at receptors in the central nervous system (Rabasseda, et al., *Toxicon,* 26:329–326, 1988). Additionally, Botulinum toxin A is not believed to result in degeneration of nervous or muscular tissue and has been approved for use in certain therapies by the U.S. Food and Drug Administration.

Botulinum toxin A is also presently being tested for its ability to cause the removal of hyperfunctional lines of the face. These tests have demonstrated that Botulinum toxin A may be administered into the musculature of the face without toxic effect to produce localized relaxation of skeletal muscle that lasts as long as six months (Blitzer, et al., *Otolaryngol Head and Neck Surg.*, 119:1018–1023, 1993).

Other serotypes of the Botulinum toxin have been identified that have immunologically distinct phenotypes; i.e., serotypes B, C1, C2, D, F and G (Simpson, et al., *Pharmacol.Rev.*, 33:155–188, 1981). All of the serotypes are believed to be proteins of about 150 kDa molecular weight that are comprised of two polypeptide chains linked by disulfide bridges. The shorter of the two chains is believed to be responsible for the toxicity of the toxin, while the longer of the two chains is believed to be responsible for the penetration of the toxin into nervous tissue. Although antigenically different to some extent, the Botulinum serotypes are believed to be similar in their pharmacological actions (Brin, et al., "Report of the Therapeutics and Technology Assessment Subcommittee of the American Academy of Neurology", *Neurology*, 40:1332–1336, 1990).

In addition, like serotype A, serotypes B and E of the Botulinum toxin have been linked to cases of botulism in humans. Thus, having the same pathological activity as serotype A, serotypes B and E can be reasonably expected to have the same therapeutic activity as serotype A in the method of the invention.

Other invertebrate toxins are known, or can reasonably be expected, to share the mode of action of Botulinum toxin and/or the toxin's ability to produce reversible, flaccid paralysis of muscles where the toxin is introduced. For example, serotypes A and E of the Botulinum toxin share a substantial degree of sequence homology with the Tetanus neurotoxin produced by *Clostridium tetani* (DasGupta, et al., *Biochemie*, 71:1193–1200, 1989). Further, although the tetanus neurotoxin typically acts on the central nervous system to produce rigid rather than flaccid muscle paralysis, at least one peptide digestion fragment of the tetanus toxin (fragment Ibc, which is produced as a papain cleavage product) have been shown to act peripherally to produce flaccid paralysis (Fedinic, et al., *Boll.Ist. Sieroter Milan*, 64: 35–41, 1985; and, Gawade, et al., *Brain Res.*, 334:139–46, 1985).

Another promising exotoxin-based therapy is the use of Staphylococcal alpha-toxin to stimulate the production of a naturally occurring brain component known as muscle-relaxing factor (MRF). Recently, researchers injected 1 microgram of Staphylococcal alpha-toxin into mice and detected elevated levels of MRF in serum and brain tissue. Reversible, flaccid paralysis of skeletal muscle in the injected mice was also observed (Harshman, et al., *Infect.Immun.*, 62:421–425, 1994), indicating that *S. alpha*-toxin also shares the mode of action of Botulinum toxin.

Reversible, flaccid paralysis has also been observed following intrathecal injection of acylpolyamine toxins, anticholinergic, presynaptic neurotoxins that are produced in the venom of many invertebrates (Herold, et al., *Anesthesiology*, 77:507–512, 1992). In particular, two toxins (AR636 and AG489) from spiders *Argiope aurantia* and *Agelenopsis aperta* have been shown to produce motor inhibition at a dosage of 2 micrograms while 7 micrograms was an effective dosage to produce sensory inhibition. Despite the apparent effects of such exotoxins on motor and sensory activity in mammals, the use of such toxins in humans to date has been limited. Further, proposals for additional applications for exotoxins use have not included extramuscular applications generally or use in reduction of headache pain specifically.

SUMMARY OF THE INVENTION

The invention provides a method for reducing headache pain and symptoms in mammals, particularly humans. Specifically, the invention comprises administering a therapeutically effective amount of a pharmaceutically safe invertebrate presynaptic neurotoxin to a mammal. The preferred routes of administration are by extramuscular injection, such as into the perimuscular areas of the face, cranium and neck, as well as into localized sites of pain in these areas. Additional therapeutic benefits can be expected from administering the presynaptic neurotoxins of the invention into one or more striated muscles of the face, cranium and/or neck (including muscles of the shoulder region) muscles in the back.

The presynaptic neurotoxins of the invention will be those neurotoxins that can be administered to a mammal to produce localized paralysis of musculature that is reversible (although such paralysis need not necessarily be induced in the practice of the invention) and does not result in degeneration of muscle or nervous tissue. The preferred presynaptic neurotoxin of the invention is Botulinum toxin A.

Surprisingly, the method of the invention may not only be applied to reduce headache pain associated with muscle spasm or contraction, but may also be utilized to reduce headache pain associated with vascular disturbances, neuralgia and neuropathy. Even more surprisingly, it has been discovered that reduction of headache pain (particularly vascular headache pain) can be achieved through extramuscular administration of the presynaptic neurotoxins of the invention; i.e., without producing flaccid paralysis of muscle. The method may also be used to reduce symptoms associated with certain kinds of headache pain, such as the premonitory aura experienced by many migraine sufferers.

DETAILED DESCRIPTION OF THE PREFERRED EMBODIMENTS

A. PRESYNAPTIC NEUROTOXIN COMPOSITIONS FOR USE IN THE METHOD OF THE INVENTION

"Presynaptic neurotoxin" as used in this disclosure refers to both invertebrate toxins and biologically active peptide fragments of proteinaceous invertebrate toxins. The presynaptic neurotoxins of the invention will be those neurotoxins that are known to produce localized, flaccid paralysis of musculature in mammals that is reversible and does not result in degeneration of muscle or nervous tissue.

It will be appreciated, however, that the reduction of headache pain which may be achieved according to the method of the invention is apparently independent of the induction of flaccid muscular paralysis which the presynaptic neurotoxins of the invention will produce. Specifically, as described further below, reduction of headache pain may be achieved at dosages of presynaptic neurotoxin which are lower or higher than dosages required to produce flaccid paralysis of skeletal muscle and without introduction of the neurotoxin into muscle tissue.

The preferred presynaptic neurotoxin of the invention is Botulinum toxin. Serotype A of this toxin is commercially available and is presently supplied by Allergan, Inc. of Irvine, Calif. under the tradename "BOTOX and by Porton Products Ltd, of the United Kingdom under the tradename "DYSPORT". A pentavalent toxoid of all eight known Botulinum serotypes is also available as an investigational drug from the U.S. Center for Disease Control in Atlanta, Ga. Of these, the Botulinum A toxin preparations are most preferred for their known safety and efficacy.

Tetanus toxins for use as vaccines are also commercially available (from, for example, Lederle Laboratories of Wayne, N.J. under the tradename "TETANUS TOXOID PUROGENATED"). As discussed above, the Ibc fragment of the Tetanus toxin is believed to act peripherally and is therefore likely to be similar in its activity to Botulinum toxin. Therefore, the method of the invention will preferably encompass the use of pharmaceutically safe forms of the Ibc fragment of the Tetanus toxin rather than the use of intact Tetanus toxin.

Those of ordinary skill in the art will know, or can readily ascertain, how to obtain the presynaptic neurotoxins of the invention, including the Botulinum and Tetanus toxoids, in a pharmaceutically safe form; preferably, a form that is nontetragenic and does not induce a detectable immune response to the toxin antigen. For most of the presynaptic neurotoxins of the invention, pharmaceutical safety will be dose-dependent such that relatively low dosages of toxin will be "safe" as compared to dosages which are known to be sufficient to produce disease.

Preferably, the presynaptic neurotoxins of the invention will be administered as a composition in a pharmaceutically acceptable carrier. To that end, presynaptic neurotoxin compositions are prepared for administration by mixing a toxin the desired degree of purity with physiologically acceptable sterile carriers. Such carriers will be nontoxic to recipients at the dosages and concentrations employed. Ordinarily, the preparation of such compositions entails combining the presynaptic neurotoxin with buffers, antioxidants such as ascorbic acid, low molecular weight (less than about 10 residues) polypeptides, proteins, amino acids, carbohydrates including glucose or dextrins, chelating agents such as EDTA, glutathione and other stabilizers and excipients. Such compositions may also be lyophilized and will be pharmaceutically acceptable; i.e., suitably prepared and approved for use in the desired application.

Most preferably, the presynaptic neurotoxin will be formulated in unit dosage form for ease of administration. For example, the presynaptic neurotoxin may be supplied as a sterile solution or lyophilized powder in a vial.

METHODS FOR ADMINISTRATION OF THE PRESYNAPTIC NEUROTOXINS OF THE INVENTION

Generally, the dose of presynaptic neurotoxin to be administered will vary with the age, presenting condition and weight of the mammal to be treated. The potency of the presynaptic neurotoxin will also be considered. Toxin potency is expressed as a multiple of the $LD_{50}$ value for a reference mammal, usually a mouse. Where a mouse is the reference mammal, one "unit" of toxin is the amount of toxin that kills 50% of a group of mice that were disease-free prior to inoculation with the toxin. For example, commercially available Botulinum toxin A typically has a potency such that one nanogram contains about 40 mouse units. The potency in humans of the Botulinum toxin A product supplied by Allergan, Inc. under the registered trademark "BOTOX" is believed to be about $LD_{50}$=2,730 units.

Assuming a potency which is substantially equivalent to $LD_{50}$=2,730 units, the presynaptic neurotoxin can be administered in a dose of up to about 1,000 units, although individual dosages of about 15–30 units are preferred and dosages of as low as about 2.5 to 5 units will have therapeutic efficacy. Generally, the presynaptic neurotoxin will be administered as a composition at a dosage that is proportionally equivalent to about 2.5 cc/100 units. Those of ordinary skill in the art will know, or can readily ascertain, how to adjust these dosages for presynaptic neurotoxin of greater or lesser potency.

Preferably, the lowest therapeutically effective dosage (i.e., the dosage which results in detection by the patient of a reduction in the occurrence and/or magnitude of headache pain experienced by the patient, even though other symptoms associated with the pain, such as the premonitory aura associated with vascular headache, may persist) will be injected. In the initial treatment, a low dosage may be administered at one site to determine the patient's sensitivity to, and tolerance of, the neurotoxin. Additional injections of the same or different dosages will be administered as necessary. For example, if headache pain predominates in the frontal cranial region (see, FIG. 1), the patient may receive up to 40 units in the glabella region, and may also receive up to 40 units of the neurotoxin in the mid-forehead region. For headache pain which predominates temporally, laterally and/or suboccipitally, the initial dosage (to be administered extramuscularly) will usually be somewhat lower; e.g., about 10 units per site, followed by up to 40 units per side.

For many indications (particularly vascular headaches), extramuscular injection will be the most efficacious route of administration as well as a route which avoids the risk of trauma to muscle tissue. Such injection may, for example, be made subcutaneously or, preferably, perivascularly (to produce infiltration of the neurotoxin into tissue at the target site). If possible, such injections will be made at a localized site of pain associated with the patient's presenting condition ("target site"); e.g., temporal, frontal and/or suboccipital sites in vascular headaches. Those of ordinary skill in the art will be familiar with such target sites and their pathological relationship to headache pain. For example, localized sites of pain known to be associated with the onset of migraine are the oculo-frontal-temporal area of the face and the forehead, with the former predominating in the early stages of migraine onset (see, e.g., Sjaastad, et al., *Func.Neurol.*, 8:27–32, 1993 [fronto-temporal pain is a typical trait of classical migraine]; this reference is incorporated herein by this reference to illustrate knowledge in the art regarding localized sites of headache pain). Common target sites are identified in FIG. 1.

Figure 1:
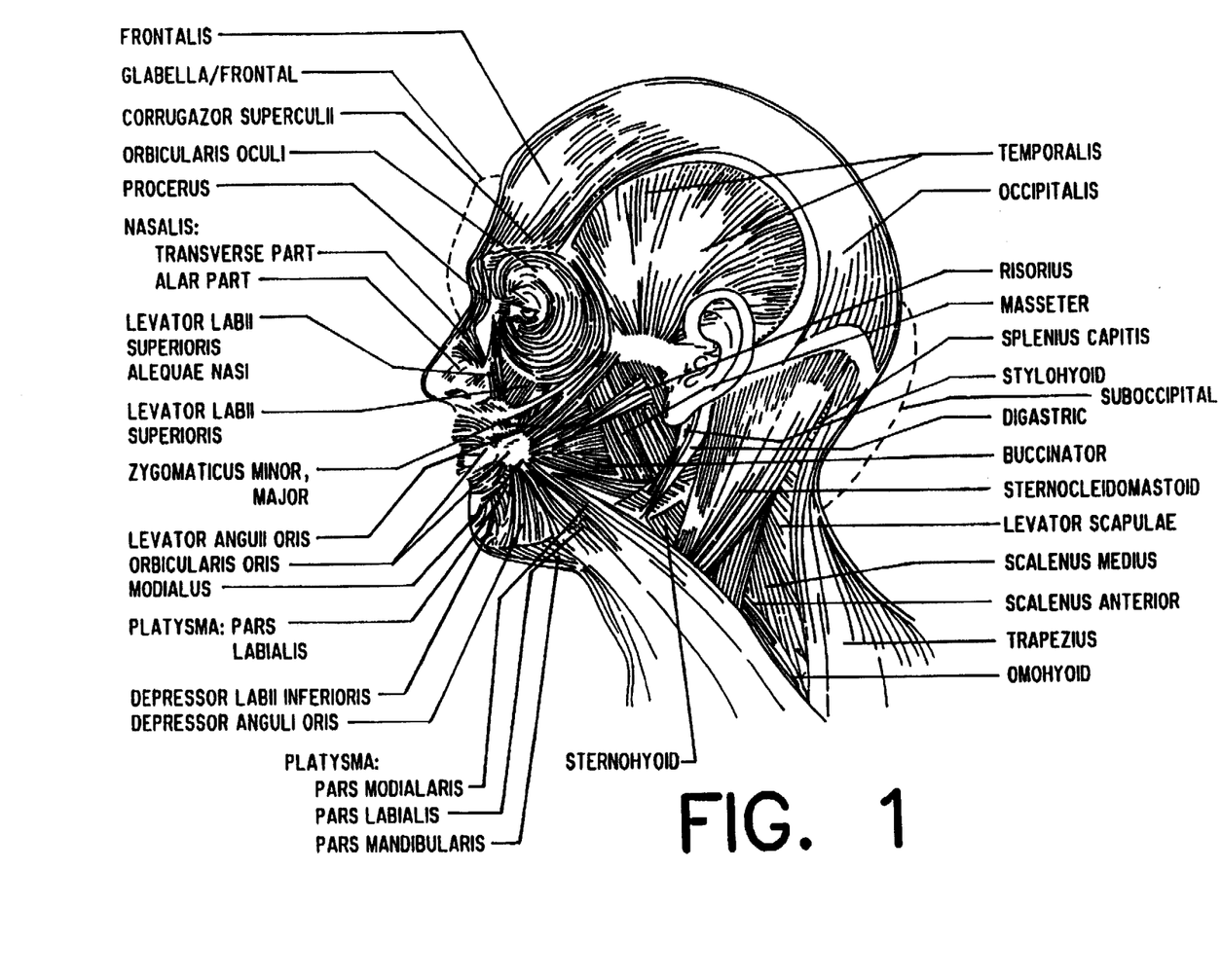
FIG. 1 is a anatomical drawing depicting the musculature of the human face, cranium and neck. Common target sites (i.e., areas of localized headache pain) are circled; (1) is the frontal and glabella region, (2) is the temporal (right) region, and (3) is the suboccipital region.

The preferred target site for injection of the presynaptic neurotoxin will be in or near the or extramuscular regions, in particular, target sites of the face, cranium and neck (see, FIG. 1). Although the precise mechanism by which the method of the invention reduces headache pain is not known, it is believed that the efficacy of the method is not necessarily dependent on whether muscle spasm or strain is present in the patient or causally related to the headache pain experienced by the patient.

For example, as shown in the data presented in the Examples, the method of the invention was effective in reducing headache pain even in persons who only received an extramuscular injection of presynaptic neurotoxin. Moreover, reduction of headache pain was unexpectedly observed even in patients whose pain was causally related to vascular or neurological components; e.g., classical migraine, trigeminal neuralgia and trauma headache. However, those of ordinary skill in the art will recognize that additional therapeutic benefits may be achieved through introduction of the presynaptic neurotoxins of the invention into musculature (particularly in the back) where muscle spasm or strain is present.

The most preferred target sites are the bilateral temporal, frontal, glabella, and suboccipital areas of the face (see, FIG. 1). The corrugator, procerus, temporal and frontalis muscles are also suitable sites for introduction of the presynaptic neurotoxins of the invention. Localized paralysis in any injected muscle can be monitored visually, by the patient's description of post-injection mobility at the target site musculature, as well as by electromyographical signals obtained at the time of administration of the neurotoxin. For introduction into extramuscluar target sites, the presynaptic neurotoxins of the invention will conveniently be administered by injection.

For intramuscular injections, to ensure that the presynaptic neurotoxin is delivered to the target site without substantial systemic distribution, the use of electromyographical ("EMG") injection is recommended. A preferred technique for EMG injection is to introduce the presynaptic neurotoxin through a monopolar hollow bore needle (commonly, one which is coated with a non-stick surface such as "TEFLON", a trademarked product of DuPont Nemours, of Massachusetts). The needle is placed through the skin and into the target site of a muscle, preferably at a neuromuscular junction. Once the needle has been inserted, the most active site of the muscle can be determined by observation of the EMG signal. Those of ordinary skill in the art will know of, or can readily ascertain, other suitable techniques for administering EMG injections.

The injections will be repeated as necessary. As a general guideline, Botulinum toxin A administered into or near muscle tissue according to the method of the invention has been observed to produce flaccid paralysis at target site muscles for up to about 3 to 6 months. Reduction of headache pain in patients who received the presynaptic neurotoxins of the invention extramuscularly has also persisted for extended periods of time. However, Botulinum A toxin in particular is expected to be most effective when administered according to the method of the invention at about 3 month intervals.

The invention having been fully described, examples illustrating its practice are set forth below. These examples should not, however, be considered to limit the scope of the invention, which is defined by the appended claims.

In the examples, the abbreviation "min" refers to minutes, "hrs" and "h" refer to hours, "mo" and "mos" refers to months, "yr" and "yrs" refer to years, and measurement units (such as "ml") are referred to by standard abbreviations. Also, "F" refers to female and "M" refers to male. Further, in Examples I and II, the following symbols indicate trademarks of the companies listed below:

■ Trademarked product of Sandoz Pharmaceuticals.

■ Trademarked product of Bristol-Myers Laboratories
■ Trademarked product of Stuart Pharmaceuticals
■ Trademarked product of Syntex Pharmaceuticals
■ Trademarked product of Merck, Sharp & Dohme Pharmaceuticals
■ Trademarked product of Schering Drug
* Trademarked product of Winthrop-Breon
○ Trademarked product of Eli Lilly Pharmaceuticals
■ Trademarked product of Roche Products
† Trademarked product of DuPont
■ Trademarked product of Ayerst Pharmaceuticals
i Trademarked product of Cerenex Pharmaceuticals

EXAMPLE 1

ADMINISTRATION OF BOTULINUM TOXIN A TO REDUCE HEADACHE PAIN IN HUMANS

Over a period of 6 months, 162 patients received 1 to 2 injections of Botulinum toxin A ("BOTOX"), reconstituted with saline to a concentration of 2.5 cc/100 units. The toxin was administered intramuscularly by EMG injection into the frontalis, corrugator, procerus and/or platysma muscles of the face. The patients were participants in a clinical trial of the use of Botulinum toxin A to temporarily remove facial wrinkles.

Of the patients who received the injections, 11 spontaneously reported a prior case history of headache pain ("headache group" patients). Of the headache group patients, 5 had a prior history of migraine, 1 had previously been diagnosed as having trigeminal neuralgia, and the remainder suffered from frequent "tension" headaches (i.e., at an occurrence of at least 3 times a week). Of the patients reporting a prior history of migraine, two reported that they were suffering from an attack at the time that the injection was administered. One of these patients was experiencing headache pain, while the other was experiencing premonitory symptoms of migraine; i.e., a visual aura. The patient with trigeminal neuralgia had previously been treated pharmacologically without substantial reduction of her symptoms.

All of the 11 patients in the headache group reported that they were either free of headaches or suffered substantially reduced headache pain (as evaluated subjectively by the patient) for periods of up to 6 months following treatment. The two patients who had reported that they were experiencing migraine symptoms at the time of treatment reported that the symptoms completely dissipated after 1 to 1½ hrs.

Additional details of the case history, treatment, and post-treatment history of patients within the headache group who agreed to the provide such information are tabulated below in Table 2.

TABLE 2

| Age/Sex | Presenting Condition | Prior Treatment | Site of Delivery | Dosage and Frequency of Injection | Post Injection Condition |
|---|---|---|---|---|---|
| 42/F | Periodic migraines over 7-8 years | CAFERGOT■ (ergotamine tartrate) | Corrugator and procerus | 12 units, 1 time; 15 units, 1 time. Administered over a 7 mos interval. | No migraine pain for 7 mos |
| 42/F | Severe migraine, at about 2 week inter- | STADOL■■ (butorphanoltartrate) | Corrugator and | 16 units, 3 times; 22 units, | No migraine pain for 3 |

TABLE 2-continued

| Age/ Sex | Presenting Condition | Prior Treatment | Site of Delivery | Dosage and Frequency of Injection | Post Injection Condition |
|---|---|---|---|---|---|
| | vals since age 8 years | analgesic and ELAVIL■■■ 4 times/day (anti-depressant) and NAPROSYN■■■■ at 500 mg/day (anti-inflammatory) | procerus | 2 times. Administered over a 3 mos interval. | mos.; one attack ended 1 h, 15 min after dosing; on 2nd occasion pain at end of migraine cycle ended 30 min after dosing |
| 38/F | Migraine sufferer, no detail available re history | No detail available | Corrugator and procerus | 16 units, 1 time; 20 units, 1 time. Administered over about a one mos interval. | No migraine pain for more than six months |
| 44/F | Tension headache about 1/week for 10 years. Most pain in left temporal region. Some joint pain on left side of jaw. | Acetaminophren (500 mg) | Corrugator, procerus and frontalis | 16 units, 1 time to the frontalis; 15 units, 1 time to the corrugator and procerus. Administered at the same time. | No headache pain for 3 months in left temporal region. Joint pain also relieved but pain occurred once in the right temporal region |
| 36/F | Daily tension headaches of moderate to severe intensity for more than 4 years | INDOCIN SR■■■■■ (75 mg) (indomethacin) | Corrugator and procerus | 16 units, 1 time | Some reduction of pain |
| 47/F | Migraine at about 1–2 month intervals and tension or sinus headache daily | Analgesic tablets, VANCEN-ASE■■■■■ (beclomethasone) | Corrugator and procerus | 16 units, 2 times to the corrugator and procerus; 12 units, 1 time to the corrugator and procerus; 20 units, 1 time to the bilateral temporal areas. Administered over a 4 mos interval. | No migraine for 4 months. Other headache pain down to about 3 day intervals |
| 41/F | Migraine at about 6 week intervals with premonitory aura and tension headache at about 1/week intervals | Codeine | Corrugator and procerus | 1 dose of 16 units. | No migraine for one month but other headache pain more frequent |
| 40/F | Tension headaches several times a week | Aspirin | Corrugator and procerus and frontalis | 15 units, 3 times corrugator and procerus; 20 units, 1 time, frontalis; 10 units, bilateral temporal areas. Administered over a 6 mos interval. | No headache pain for one year |
| 58/F | Tension headache associated with premenstrual cycle | Ibuprofen | Corrugator, procerus and frontalis | 10 units, 1 time to corrugator and procerus; 16 units, 2 times to corrugator and procerus; 16 units, 1 time to frontalis; 20 units, 1 time to frontalis. Administered over a 5 month period. | No headache pain for approximately 3 mos. |

Additional patients ("pt.") were treated using the method described in Example I, with particular emphasis on extramuscular injections of the Botulinum A toxin in the frontal, suboccipital and temporal regions of the face. The only adverse effect of the injection reported by any patient was soreness at the injection site, particularly at intramuscular injection sites. The results of the treatment received by each patient are reported in Table 3, below.

TABLE 3

| Age/Sex | Prior Treatment | Site of Delivery | Presenting Condition | Post Injection Condition |
|---|---|---|---|---|
| 42/F | ■Cafergot | 12 units, Glabella 5/7/93; 5 units, Glabella 10/29/93 | Has had severe headaches (possibly of migraine origin) for the last 7-8 years without premonitory symptoms. Bright lights, loud noises, dairy products intensify pain. | As of 11/93: the pt. was quoted as saying: "Since I received the BOTOX, almost 6 months ago, my migraines [headaches] have been completely eliminated." NOTE: Most of the pt.'s corrugator muscle function returned 3 months after the injection, although pt. had has not had headache pain for another 3 after muscle function returned. |
| 42/F | Stadol■ ■ now. In past - Cafergot■ | 16 units, Glabella 10/23/92; 16 units, Glabella 6/11/93; 10 units, Forehead 6/30/93; 6 units (booster), Glabella 6/30/93; 22 units, suboccipital (left side) 1/13/94; 22 units, suboccipital (right side) 4/13/94; 20 units each, Glabella and Bilateral Temporal 6/10/94; 10 units each, Left parietal, left and right suboccipital 9/14/94; 10 units left suboccipital and 20 units bilateral temporal 9/30/94 (Forehead, bilateral temporal and suboccipital injections not into muscle). | Onset - 8 years of age; Cheese/Chocolate/Stress - set off headaches (possibly of migraine origin); Symptoms: Pain "severe", nausea; Frequency: Every 2 weeks until head injury, 7/94. Frequency increased, with additional parietal and suboccipital pain not experienced in past migraine history. | Pt. had a migraine when treated on 4/13/94. Within 30 min. nausea ended; within 1.5 hours the migraine pain ended. No migraine headache pain for 3 months after each treatment. NOTE: Flaccid paralysis of the corrugator and procerus muscles was achieved on June 11, 1993. However, elimination of pain was not achieved until injections given on 6/30/93. Elimination of headache pain in the left suboccipital region achieved on 1/13/94; elimination of pain in the right suboccipital region achieved 4/13/94, Pain associated with head injury relieved within several hours of injection. However, pt. reports occasional occurrence of nausea. |
| 38/F | 4-5 ibuprofen and other drugs | 16 units, Glabella 3/25/94; 20 units, Glabella 4/15/94 16 units, Glabella 6/29/94 | Pt. began experiencing frequent severe headache pain (possibly of migraine origin) without premonitory symptoms about 9 years ago. | As of receiving first injection, pt has not had any headache pain for about 6 months. However, the second injection was required to induce flaccid paralysis of muscle. |
| 44/F | Acetomenaphin, 500 mg. | 15 units, Glabella 2/18/94; 16 units, Forehead 2/18/94; 23 units, Forehead 9/9/94 (Forehead injection not into muscle). | Suffers severe headaches (possibly of migraine origin) about once a week for last 10 years. Intensity ranges from moderate to extreme. Most headaches appear to be centered in the left temporal area. No premonitory symptoms. Pt. also reported experiencing some pain in the temporal | Pt. had one headache in the right temporal area in March, 1994. Otherwise, for about 7 months following the first set of injections, pt. did not experience any headache pain over her forehead and upper frontal cranial region. However, pt. |

TABLE 3-continued

| Age/Sex | Prior Treatment | Site of Delivery | Presenting Condition | Post Injection Condition |
|---|---|---|---|---|
| | | | mandibular joint area. | reported having premonitory nausea and other symptoms of migraine. TM Joint pain also relieved on left side of face. |
| 36/F | Elavil ■■■-25 mg. 4 times a day; Naprosyn ■■■-500 mg. daily; Indocin ■■■■: 75 mg. | 16 units, Glabella 3/25/94 | Pt. suffers from moderate to severe headaches daily. Pt was diagnosed with chronic tension headaches 4 years ago by a neurologist. Pt. had been in several car accidents before experiencing the diagnosed condition. Pt. does not experience premonitory symptoms. | Pt. described condition as being a "minor improvement" of her headache pain. |
| 47/F | Aspirin;Vancenase ■■■■■ | 16 units, Glabella 1/27/94; 12 units, Glabella 4/15/94; 20 units, Crow's 4/15/94; 15 units, Glabella 8/24/94 (Crow's feet area injection not into muscle) | Onset: 12 years of age, Precipitating Events: Strong odor/heat/bright lights/noises/being startled/and hunger. Hands can become cold or tingling sensations can occur. Becomes nauseated. Occurrence: "Migraine" (severe) headaches - once every 1–2 months. Other type of "general" (tension) headache occurs daily. Relief: Vanconase Inhaler (for vasomotor rhinitis)/quiet, dark room. | Pt. reports that she has not had a severe ("migraine") headache since the treatment began. Pt. also reports that she has "general" headache pain only "sporadically" (e.g., decreased in frequency from daily to approx. every 3 days). |
| 44/F | Aspirin | 16 units, Glabella 4/15/94; 12 units, Glabella 5/27/94 | Onset: early 30's. Tension headaches nearly every morning. On a scale of 1–10, patient rated her headaches 3–4. | During the period between receiving the first and second injections, pt. reports that she did not have any headache pain. Pt. did have a headache on the morning of 5/27/94 (date of 2nd injection) which was relieved by aspirin. |
| 41/F | Codeine tablets | 18 units, Glabella 4/15/94 | Onset: 12 years of age after head trauma. Diagnosed as having migraine headaches triggered by certain smells and muscle spasms. Has premonitory aura which lasts for 20–25 minutes. Headache pain occurs with hot flashes, visual disturbances and excessive perspiration. Occurs approximately every 6 weeks. Pt. also reports have less frequent tension headaches. | Pt. reports that she did not experience any migraine headache pain for about 3 months, but is having more frequent tension headaches. Pt.'s ability to contract injected muscles returned before she experienced another migraine headache. Note: Patient came into office with migraine headache. Within 1 hour after injection, the symptoms were relieved. |
| 40/F | Aspirin | 10 units, Crow's feet area 10/6/93; 15 units, Glabella 10//93; 20 units, Forehead 10/6/93; 20 units, Crow's feet 4/25/94; 8 units, Chin 4/25/94; 20 units, Crow's feet 5/27/94; 15 units, Crow's feet 7/15/94 | Frequent headaches (probably tension headaches). | Since injections given over the course of last 6 months, pt. reports that she has not had any headache pain for approximately 1 year. |

TABLE 3-continued

| Age/Sex | Prior Treatment | Site of Delivery | Presenting Condition | Post Injection Condition |
|---|---|---|---|---|
| | | (Forehead and Crow's feet area injections not into muscle) | | |
| 48/F | Acetominephren, Ibuprofen | 10 units, Glabella 3/8/93; 16 units, Glabella 10/29/93; 16 units, Crow's feet 10/29/93; 20 units, Crow's feet 3/25/94; 16 units, Glabella 8/3/94; 20 units, Crow's feet 8/3/94; 20 units, Glabella 10/24/94 (Forehead and Crow's feet injections not into muscle) | Headache pain (possibly of migraine origin) associated with onset of menstrual cycle. | Without headache pain for the almost 1½ years since the first injection. Pt. reported that her headache symptoms had diminished before flaccid paralysis of injected muscles was induced. Pt. experienced mild headache pain at left temporal site 3 days before injection on 10/24/94. |
| 41/F | Inderal (propanolol HCL)■ | 20 units, Glabella 5/6/94; 14 units, Medial Forehead 5/6/94; (Latter injection not into muscle) | Daily headaches for past 7 years. True migraine headache - once every 3 to 6 months. | No follow up report yet available. |
| 57/F | 2 Tablets Fiorinal (butalbinal) w/Codeine. | 10 units, Crow's feet 12/4/92; 20 units, Crow's feet 3/25/94; 15 units, Glabella 3/25/94 (Crow's feet injection not into muscle) | Pt. described headache pain as "a crushing" pain in the forehead and temporal areas that occurs about 1 time/week and is associated with eye strain. | On 3/25/94, pt. reported having no headache pain for first 7 weeks after receiving the first injection. She reported having 1 headache in the 8th week which was "weaker" in severity than headache pain she recalled having prior to receiving the injections. |
| 43/F | Aspirin | 12 units, Glabella 3/18/94; 24 units, both sides, Glabella (+4 units to both sides, Glabella area) 3/4/94; 36 units, Forehead 6/7/94; 8 units, Lateral Glabella 6/29/94; 20 units, Crow's feet 8/24/94; 16 units, Glabella 9/30/94; 12 units, Medial Forehead 9/30/94 (Crow's feet and forehead injections not into muscle) | Daily headache pain brought on by stress. | Pt. states that for first 6 weeks after Botox injection on March 4, 1993, she did not experience any headache pain. Pt. had "a few" headaches after first 6 weeks, but described them as "much weaker" in severity. However, once muscle mobility (glabella) returned, the frequency of the patient's headaches increased. |
| 50/F | Acetominephren, cold compresses to forehead; lie down in dark room | 10 units, Glabella 2/22/93; 12 units, Glabella 5/7/93; 15 units, Glabella 11/5/93; 16 units, Glabella 5/27/94 | Onset: Age 20. Frequency: Regular headaches 3 times per week. Migraine headache - 1 time per month with premonitory auras. | Pt. reports that for 6 months after receiving the first injections she did not have any headaches. |
| 41/F | Fiorinal and Fiorinal with Codeine■; Demerol (meperidine HCL)● at hospital with severe attack | 18 units, Glabella 6/29/94 | For the last 7–8 years pt. had migraine headaches several times per month with premonitory aura. | 3 months after receiving the injection, pt. reports that she has not had a migraine. However, pt. has had 3 headaches which she describes as "mild". |
| 41/F | Aspirin | 18 units, Glabella 3/9/94; 20 units, Glabella 7/15/94 | Headaches 1 time a week of moderate severity. Area of headache = over frontal region and forehead. | 6 months after receiving the first injection, pt. reports that she has not experienced a headache. |
| 47/F | Ibuprofen | 17.5 units, Glabella 8/3/94; 20 units, Crow's feet 9/30/94; 20 units, Bilateral Temporal 9/30/94 | Frequent headaches described as a dull ache over forehead, temporal areas and back of head. Pt. also reports some pain in the | Patient complained of headache at injection site for first 2 days. As of 9/16/94, still having daily headaches. |

TABLE 3-continued

| Age/Sex | Prior Treatment | Site of Delivery | Presenting Condition | Post Injection Condition |
|---|---|---|---|---|
| | | (Crow's feet and temporal injections not into muscle) | temporal mandibular joint. | However, patient states a decrease in severity. She still has movement in the glabella area. As of 10/7/94: After injection on 9/30/94 (given to temporal region), pt. reports headache in forehead area eliminated. TMJ pain also described as being "improved". |
| 37/M | Aspirin; acetominephen; Percodan (oxycodone HCL)† | 20 units, Crow's feet 10/23/92; 29 units, Crow's feet 3/18/93; 8 units, Crow's feet 7/9/93; 17.5 units, Glabella 7/9/93; 20 units, Crow's feet 11/11/93; 15 units, Glabella 12/22/93; 18 units, Glabella 8/3/94; (Crow's feet injections not into muscle) | Age of onset: 28 years. Frequency: about 2 times a week. Signs and Symptoms: Patient reports that she feels pain in her forehead and back of head. Measures taken for relief: dark room, cold compresses, Aspirin, Tylenol, Percodan. | As of 10/7/94: pt. reports having a "mild" headache once every few weeks after receiving first injection. |
| 54/F | Imitrex (sumatriptan succinate) ¡; Darvon (propoxyphene HCL)○. Taking Imitrex during treatment | 16 units, Glabella 8/26/94; 10 units, Right Suboccipital 9/30/94; 20 units, Bilateral Temporal 9/30/94; 10 units, Left Suboccipital 9/30/94 (Latter three not into muscle) | Age of onset: 4 years. Frequency: Daily. Diagnosed as migraine. Precipitating events: heat, using computer, chocolate, stress, allergies to pollen. Signs and Symptoms: Pain in back of neck and flashing lights. Reports 12+ pain on scale of 1-10 when she doesn't take Elavil 25 mg. (Note: patient was using Imitrex daily + 2 Darvons + 10 mg of Valium daily which would give minimal relief to headache). | As of 9/16/94: After initial injection pt. reported a general decrease in headache intensity and no headache pain in glabella area. After second injections (R. suboccip.), patient reported decrease in headache pain at injection site (back of neck on that side) and a further decrease in pain intensity in other areas (i.e. back of eyes and other side of neck). Patient is no longer using Imitrex for pain relief. Has used Darvon or Valium to relieve headache pain only once since last injection and reports that she no longer experiences the onset of migraine on exposure to a precipitating event. |
| 45/F | Codeine, Demerolo, Fiorinal■, acetominephen | 15 units, Glabella 9/1/94; 15 units, Forehead 9/1/94; 20 units, Bilateral Temporal 9/30/94 (Latter two not into muscle) | Regular (diagnosed) migraines and frequent tension headaches. Precipitating events: Various things will bring on headaches, such as certain smells, weather changes, cold, etc. | As of 9/16/94: no migraines since temporal injection. However, pt. reports that she still has tension headaches, though describes them as being relatively "mild". |
| 26/F | Dalmane (flurazepam HCL)∗ | 18.5 units, Glabella 8/24/94; 20 units each, Glabella and Bilateral temporal (latter not into muscle). | Onset: Age 16. Regular (diagnosed) migraines and less frequent tension headaches. Headache located in forehead and in back of ears. Pt. experiences classic migraine aura, nausea, vomiting, loss of consciousness at times. Pain radiates over left side of head. | As of 9/19/94 Pt. reported that she still has tension headaches with neck pain, but no forehead pain. Pt. also reports that she has not had a migraine headache since receiving the injection. As of 10/10/94, forehead pain returning. On 10/20 |

TABLE 3-continued

| Age/Sex | Prior Treatment | Site of Delivery | Presenting Condition | Post Injection Condition |
|---|---|---|---|---|
| 28/F | Imitrex | 16 units, Glabella 9/30/94; 20 units, Bilaterally into the Crow's feet area 9/30/94 (latter injections not into muscle) | 2 different types of headaches. (1) general headache 2-3 times per week. Starts behind eyes and radiates to back and top of head. (2) migraine: diagnosed as migraine at age 13. Frequency: 2 times per month. Starts behind eyes and radiates behind neck. It starts with shiny lights and visual disturbances with classic aura's. If she can take medication prior to onset it may stop it from proceeding to a full cycle. | had severe pain in right temporal area, nausea, blurred vision. About 2 hrs. after injections on 10/20, pain and related symptoms gone. 11/11/94: Patient states that she had no headache since the treatment. |
| 21/F | Aspirin | 20 units, Glabella 9/20/94 | Pt. has suffered from periodic migraine with light intolerance, nausea and blurred vision for several years, as well as more moderate tension headache pain. Pain primarily localized in frontal and temporal areas. | Since injection, pt. reports that she has not experienced any headache pain. |
| 49/F | Cafergot; Codeine; Antidepressants; Beta blockers (taking during treatment) | 20 units, Glabella 9/30/94; 20 units, Bilateral Temporal 9/30/94; 11/9/94, 20 units, Left Temporal (Latter two injections not into muscle) | Patient has suffered from "vascular migraines" for over 21 years with pain primarily on the right side of her head. Precipitating events: Strong smells, bright lights, certain foods such as cheese, herring thyramine-containing foods, red wine, chocolate, caffeine. Aura and stuffy nose. Symptoms: dizziness, nausea, pain. | As of 10/14/94, pt. reports that she had a migraine on 10/6 without premonitory symptoms that she described as "diminished". However, pt. reported having a severe migraine on 10/12, but stated that the pain was only on the left side of her head. Pt. reported that she has not had any cluster headache pain since receiving second injection. |

I claim:

1. A method for reduction of pain associated with a migraine headache in a mammal comprising administering a therapeutically effective amount of an invertebrate presynaptic neurotoxin in a pharmaceutically safe form to the mammal.

2. The method according to claim 1 wherein the neurotoxin is delivered to the face, cranium and neck.

3. The method according to claim 2 wherein the presynaptic neurotoxin is delivered to one or more of the frontalis, corrugator, procerus and bilateral temporal muscles.

4. The method according to claim 2 wherein the presynaptic neurotoxin is also delivered to the mammal's back.

5. The method according to claim 1 wherein the presynaptic neurotoxin is administered by electromyographical injection into the muscle.

6. The method according to claim 1 wherein the presynaptic neurotoxin is administered by injection in the area of the neuromuscular junction.

7. The method according to claim 1 wherein the presynaptic neurotoxin is a Botulinum toxin.

8. The method according to claim 7 wherein the Botulinum toxin is Botulinim toxin A.

9. The method according to claim 1 wherein the presynaptic neurotoxin is a biologically active fragment of a proteinaceous toxin.

10. The method according to claim 9 wherein the biologically active fragment is the lbc fragment of the Tetanus toxin.

11. A method for reduction of symptoms associated with the onset or presence of a migraine headache in a mammal comprising administering a therapeutically effective amount of an invertebrate presynaptic neurotoxin in a pharmaceutically safe form to the mammal.

12. A method for reduction of pain associated with a migraine headache in a mammal comprising administering a therapeutically effective amount of an invertebrate presynaptic neurotoxin in a pharmaceutically safe form to the mammal by delivery of the presynaptic neurotoxin to an extramuscular site of the face, cranium or neck.

13. The method according to claim 12 wherein the neurotoxin is delivered to one or more target sites of the migraine headache pain experienced by the mammal.

14. The method according to claim 13 wherein the presynaptic neurotoxin is delivered to one or more of the frontal, temporal and suboccipital areas of the face.

15. The method according to claim 12 wherein the presynaptic neurotoxin is administered by perivascular injection.

16. The method according to claim 12 wherein the presynaptic neurotoxin is administered by subcutaneous injection.

17. The method according to claim 12 wherein the presynaptic neurotoxin is a Botulinum toxin.

18. The method according to claim 17 wherein the Botulinum toxin is Botulinum toxin A.

19. The method according to claim 12 wherein the presynaptic neurotoxin is a biologically active fragment of a proteinaceous toxin.

20. The method according to claim 19 wherein the biologically active fragment is the Ibc fragment of the Tetanus toxin.

21. A method for reduction of symptoms associated with the onset or presence of a migraine headache in a mammal comprising administering a therapeutically effective amount of an invertebrate presynaptic neurotoxin in a pharmaceutically safe form to the mammal by delivery of the presynaptic neurotoxin to an extramuscular site in the face, cranium or neck.

* * * * *

UNITED STATES PATENT AND TRADEMARK OFFICE
CERTIFICATE OF CORRECTION

PATENT NO. : 5,714,468
DATED : February 3, 1998
INVENTOR(S) : William J. Binder

It is certified that error appears in the above-identified patent and that said Letters Patent is hereby corrected as shown below:

In column 2, lines 25-45, Table 1(b) should appear as follows:

TABLE 1(b)

HEADACHES PRIMARILY ASSOCIATED WITH DISORDERS OF THE FACIAL AND CRANIAL NERVES

| | | | |
|---|---|---|---|
| Trigeminal neuralgia | Idiopathic, vascular disturbances, multiple sclerosis, tumor | Trigeminal nerve, unilateral | Carbamazepine |
| Atypical facial neuralgia | Depressive, anxiety states, idiopathic | Unilateral or bilateral | Anti-depressant and anti-anxiety medication |
| Orbitally related neuralgias | Idiopathic, parasinus disorders | Unilateral in eye, cheek, ear, neck | Decongestant nasal medication |
| Tolosa-Hunt Syndrome | Arteritis and granulomatous lesions | Unilateral, mainly orbital | Corticosteroid therapy |
| Reader's paratrigeminal syndrome | Tumors, granulomatous lesions | Unilateral, frontotemporal and maxilla | Varies depending on origin |
| Postzoster syndrome | Herpes zoster | Unilateral, trigeminal divisions | Carbamazepine and anti-depressants |
| Costen's syndrome | Loss of teeth, rheumatoid arthritis | Unilateral, near temporomandibular joints | Bite correction, arthritis related therapies |

Signed and Sealed this

Twenty-seventh Day of June, 2000

Attest:

Q. TODD DICKINSON

*Attesting Officer*     *Director of Patents and Trademarks*